United States Patent [19]

Smither

[11] Patent Number: 5,869,841
[45] Date of Patent: Feb. 9, 1999

[54] 3-DIMENSIONAL IMAGING SYSTEM USING CRYSTAL DIFFRACTION LENSES

[75] Inventor: Robert K. Smither, Hinsdale, Ill.

[73] Assignee: University of Chicago, Chicago, Ill.

[21] Appl. No.: 762,992

[22] Filed: Dec. 10, 1996

[51] Int. Cl.$^6$ .............................. G21K 1/06; G01T 1/16
[52] U.S. Cl. ................................ 250/505.1; 250/363.04; 250/370.09; 378/149
[58] Field of Search .......................... 250/505.1, 370.09, 250/363.04; 378/149

[56] References Cited

U.S. PATENT DOCUMENTS

| | | |
|---|---|---|
| 4,429,411 | 1/1984 | Smither . |
| 5,479,469 | 12/1995 | Fraser et al. ............................. 378/149 |

FOREIGN PATENT DOCUMENTS

| | | | |
|---|---|---|---|
| 0 412 734 A2 | 2/1991 | European Pat. Off. .......... | 250/363.04 |
| 60-233600 A | 11/1985 | Japan ..................................... | 378/149 |
| 92/08235 | 5/1992 | WIPO ................................... | 250/505.1 |

OTHER PUBLICATIONS

Peter von Ballmoos et al. "A Positron Annihilation Radiation Telescope Using Laue Diffraction in a Crystal Lens" Centre D'Etude Spatial Des Rayonnements Report 94–1327, Feb. 1993. CESR—9 avenue du Colonel–Roche, 31029 Toulouse Cedex, France.

*Primary Examiner*—Constantine Hannaher
*Attorney, Agent, or Firm*—Cherskov & Flaynik

[57] ABSTRACT

A device for imaging a plurality of sources of x-ray and gamma-ray radiation is provided. Diffracting crystals are used for focussing the radiation and directing the radiation to a detector which is used for analyzing their addition to collect data as to the location of the source of radiation. A computer is used for converting the data to an image. The invention also provides for a method for imaging x-ray and gamma radiation by supplying a plurality of sources of radiation; focussing the radiation onto a detector; analyzing the focused radiation to collect data as to the type and location of the radiation; and producing an image using the data.

23 Claims, 11 Drawing Sheets

3-DIMENSIONAL IMAGING SYSTEM USING CRYSTAL DIFFRACTION LENSES

STATEMENT REGARDING FEDERALLY SPONSORED RESEARCH OR DEVELOPMENT

The United States Government has rights to this invention pursuant to Contract No. W-31-109-ENG-38 between the U.S. Department of Energy and the University of Chicago, representing Argonne National Laboratory.

BACKGROUND OF THE INVENTION

1. Field of the Invention

This invention relates to a method of imaging a source of radiation and to a device for imaging a source of radiation, and more specifically, this invention relates to a method and device for producing a three-dimensional image of a source of x-ray and gamma-ray radiation for medical and other applications by using a plurality of diffracting crystals which focus x-ray and gamma-ray radiation onto a plurality of detection devices.

2. Background of the Invention

Cancer tumor cells have high rates of metabolism and multiply rapidly. Substances injected into the body tend to migrate to locations of such high growth and become incorporated in this new growth. If the injected substance is a short-lived radioactive isotope, the location of a tumor can be detected by locating the region of high radioactivity. Aside from pinpointing tumor location, an image of the tumor is also desirable to ascertain its shape, size, and juxtaposition with adjacent structures.

One method used to detect tumors is to first inject a body with radioactive compounds such as the Technetium isotope $^{99m}$Tc, which is a 140.5 kiloelectron volt (keV) gamma emitter having a half-life of 5.9 hours. The gamma rays are detected by a large sodium iodide (NaI) scintillator crystal placed behind a collimator grid yielding at best an 8 millimeter (mm) resolution at the location of the source. The scintillator is viewed by a plurality of photomultiplier tubes and the location of a scintillation event is determined by a computer analysis of the relative intensity of the photomultiplier signals. The collimator/scintillator assembly is placed above and very close to the patient. Aside from this method yielding a low resolution of between approximately 8 mm and 1 centimeter (cm), the image produced is limited to the plane parallel to the surface of the scintillator. As such, the technique provides no depth information about the source. This deficiency can be remedied somewhat by adding another collimator/scintillator assembly below the patient, comparing the counting rate of the two scintillators, and thus estimating the position of the source along the line joining them. In the latest revision of this method the large Na I detector plus collimator is rotated around the patient, taking a plurality of images at different angles. This allows one to generate a three-dimensional image of the radiation emitting area. There are considerable additional costs associated with this method and the fact that this method has been introduced in spite of the additional costs underscores the importance of three-dimensional imaging.

Another popular imaging technique is positron emission tomography (PET), used in diagnosis and medical research. In PET, a chemical compound containing a short-lived, positron-emitting radioisotope is injected into the body. The positrons (positively charged beta particles) are emitted as the isotope decays. These particles annihilate with electrons in surrounding tissue. Each annihilation simultaneously produces two 511 (keV) gamma rays traveling in opposite directions. After passing through collimators, these two gamma rays are detected simultaneously by scintillation detectors placed at 180 degrees to each other, and on opposite sides of the patient. The signals from the detectors' photomultiplier tubes are analyzed by a computer to facilitate the production of an image of the radiation-emitting region.

Numerous drawbacks exist with scintillation detector tomography. For instance, the typical coarse resolution of no less than 8 mm often results in smaller structures being overlooked. This prevents early detection of cancerous tumors when they are least likely to have metastasized and when treatment is most likely to succeed. This is especially a disadvantage in the detection of breast cancer tumors wherein the tumors often become virulent before growing to a detectable size. Presently, mammography uses x-rays to detect tissue calcification. The assumption is made that this calcification is due to dead cancer cells and that there is a live cancer tumor in the immediate vicinity. Often however, there is no live tumor where calcification has been detected. In fact, the calcification may not have been due to a tumor at all. Unfortunately then, positive mammography results often lead to unnecessary surgical operations.

Also, because poor spacial resolution often causes images of actual small tumors to be diffuse, variations in background radiation are often mistaken for actual tumors, leading to unnecessary surgical operations. This inadvertent incorporation of background radiation is an artifact of scintillation detector use wherein the detector must be large enough to cover a given area of the body. Aside from intercepting the radiation emanating from the source under observation, however, the large detectors also detect all ambient background radiation penetrating the scintillating region and this ambient radiation is analyzed as if it had been emitted by the source under observation.

Another drawback to using imaging techniques incorporating scintillation detectors is that all of the various radiations emitted by the source are detected by the detectors. As such, a specific radiation having an energy indicative of a specific, injected isotope cannot be easily scrutinized.

Lastly, because collimators allow for the detection of only the radiation that is emitted in a very narrow direction in space, the patient has to be injected with a relatively large amount of radioactive material.

Recently, efforts have been made to improve scintillation detector tomography. Some PET instruments now achieve a resolution as small as 4 mm. Such improvements entail considerable expenditures and have the additional drawback that the improvement in resolution has come at the cost of a decrease in counting rate. This entails in turn either a longer examination time per patient or the injection of a stronger dose of radiation. Furthermore, the prospects for further improvements in resolution are limited by the fact that such improvements require collimators with ever smaller apertures, and therefore greater mass, together with lower count rates. This increase in collimator mass will increase the number of forward Compton-scattered photons in the collimators and these forward scattered photons are often indistinguishable from those emanating directly from the source.

To obtain significant improvements in spacial resolution and in detection efficiency as well as a three dimensional location of the source, a method for focusing the radiation emanating from the source is required. Laboratory instruments utilizing the phenomenon of crystal diffraction have been used to focus x-ray and gamma-ray radiation. For instance, U.S. Pat. No. 4,429,411, issued Jan. 31, 1984, to the applicant, discloses a method of focussing x-rays and gamma rays by using bent crystals, crystals that are differentially heated, and crystals that have been differentially doped with impurities. Because of the limits on the amounts of crystal bending, differential heating, or differential doping that can be achieved in practice, these methods do not allow for devices with a focal length of less than a few meters. Aside from the problems associated with situating such large devices in a medical facility and manipulating the associated large componentry thereof, the long focal length of such large devices would also result in low detection efficiencies. Therefore, the imaging patient would need to be injected with a relatively large amount of radiation.

A need exists in the art for a method and device for imaging x-ray and gamma-ray sources with sufficient spacial resolution to accurately observe structures smaller than 8 mm in size. The method and device must have sufficient energy resolution to allow the imaging of radiation of a selected energy to the exclusion of others. The method and device also must be embodied in a manageable size for easy manipulation of pertinent portions of the method or device so as to customize imaging sessions to multiple, specific radiation energies. The method and device also must limit the radiation to which the patient is exposed by incorporating a redirecting or "focussing" mechanism to detect radiation emanating from a tumor while disregarding ambient levels of radiation.

SUMMARY OF THE INVENTION

It is an object of the present invention to provide a method and a device for imaging sources of gamma-ray and x-ray radiation that overcome many of the disadvantages of the prior art.

Another object of the present invention is to provide a device for three-dimensional imaging of sources of gamma and x-ray radiation emanating from a subject. A feature of the present invention is the use of non-coplanar arrays of lenses and detectors to record data simultaneously for analysis by a computer. An advantage of the invention is the generation of the three-dimensional image of the source while the subject is under examination.

Still another object of the present invention is to provide a method for producing a high resolution image of a radiation source located in a patient. A feature of the invention is the imaging of sources less than 4 mm in size. An advantage of the invention is the obviation of unnecessary, invasive surgical procedures.

Another object of the present invention is to provide an imaging device with a high detection efficiency. A feature of the present invention is that the crystals for each lens are so altered that the condition necessary for crystal diffraction is valid over a large fraction of the crystals' area. An advantage of the invention is that the lens redirects or "focuses" onto a detector between one quarter and three quarters of the radiation emitted in the cone subtended by the lens. Another feature is that the detector is located remotely from the source and that both the volume of the detector and the exposed frontal area of the detector are small compared to the volume and the frontal area of the lens. An advantage conferred by this small detector size and by the large separation between detector and source is that the detector receives very little direct radiation from the body being examined and furthermore, that the detector can be shielded from background radiation, thereby providing a high signal to background noise ratio.

Yet another object of the present invention is to provide a radiation imaging method having a fast imaging time. A feature of the invention is the use of scintillation detectors to locate the approximate position of the radiation source and then the use of a high efficiency crystal diffraction system to produce a high resolution image of the source of from 2 mm to less than 8 mm. An advantage of the invented method is that the amount of radiation necessary to produce a high resolution image is relatively small compared to typical scintillation detector methods.

Another object of the present invention is to provide an economical and manageable imaging device. A feature of the invention is that each of its lenses is made of a plurality of small, individually mounted crystal units. Another feature of the invention is that the focal length of the lenses can be as small as 50 cm for radiation of 140 keV. An advantage of the invention is that a defective crystal in one of the lenses can be replaced quickly and at low cost. Should an individual lens become damaged in a multi-lens system, the lens can be replaced quickly and at low cost. The modular nature of the multi-lens system makes it possible to operate even though some of the crystals in a lens are damaged and even when the whole damaged lens is removed. Another advantage is that the total length of the lens/detector assembly can be as short as two meters (m).

Still another object of the present invention is to allow the imaging system to observe radiation of a selected energy to the exclusion of other energies. A feature of the present invention is that the focal length of the lens depends on the energy of the radiation. An advantage of the present invention is that the lens can be so constructed as to focus only radiation of the desired energy.

In brief the invention provides a device for imaging a plurality of sources of x-ray and gamma radiation comprising a means for focussing the radiation onto a detector; a means for analyzing said directed radiation to collect data as to the location of the source of the radiation; and a means for converting the data to an image.

The invention also provides for a method for imaging x-ray and gamma radiation comprising: supplying a plurality of sources of radiation; focussing said radiation onto a detector; analyzing said focussed radiation to collect data as to the location of the source of the radiation; and producing an image using the data.

BRIEF DESCRIPTION OF THE DRAWINGS

The present invention together with the above and other objects and advantages may best be understood from the following detailed description of the embodiment of the invention illustrated in the drawings, wherein.

DETAILED DESCRIPTION OF THE INVENTION

Figure 1:
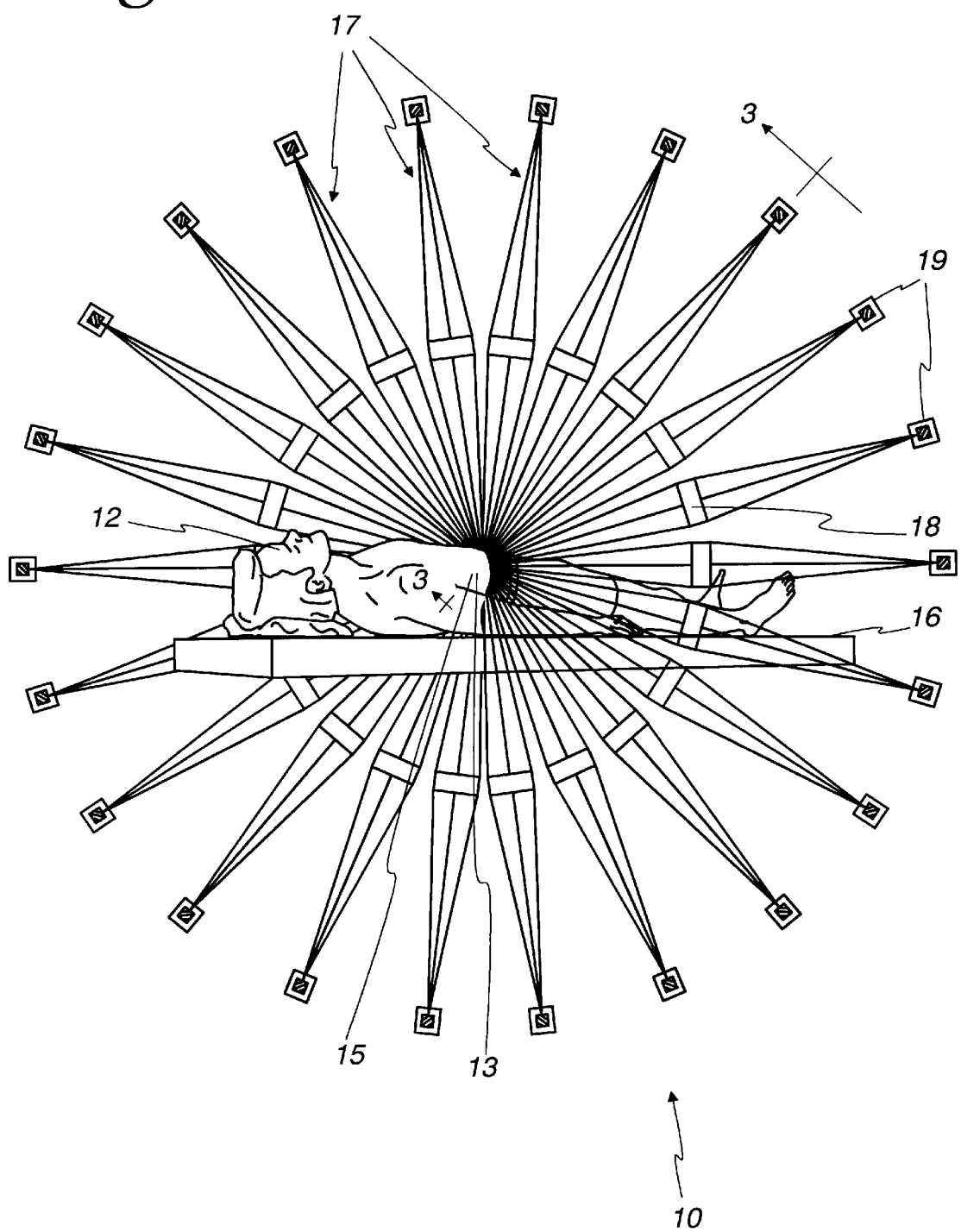
FIG. 1 is an elevational view of a single coplanar array of lens/detector assemblies in accordance with the present invention.

The present invention provides a method and a device for imaging sources of x-ray and gamma-ray radiation. The device, designated generally as numeral 10 in FIG. 1, incorporates a plurality of lens/detector assemblies 17 to first focus and then detect radiation emanating from a radioactive source 15, such as a tumor in a patient 12 that has incorporated some radioactivity as it grows. Each lens/detector assembly 17 comprises a plurality of high efficiency and high resolution crystal diffraction lenses 18 that focus onto detectors 19 only the radiation of a desired energy and origin. As disclosed infra, and with reference to FIG. 6, each lens 18 comprises a plurality of concentric rings 45, which in turn are comprised of very accurately mounted diffracting crystals. These crystals are oriented so that only radiation having a predetermined energy is focused onto the detector 19. The detectors 19 of the device are shielded from unwanted radiation.

The device 10 is designed to accommodate the detection of radiation from a myriad of sources. For clarity, the radiation source 15 in the exemplary embodiment shown in FIG. 1 is a tumor that has absorbed a radio-isotope in vivo, whereby the tumor emits radiation of a predetermined wave length $\lambda$. However, other radiation sources are also appropriate, including radioisotope-impregnated fissures in a mineral or in a manufactured object, an x-ray or gamma-ray beam scattering from a target, x-rays or gamma rays produced by particle-beam bombardment of a target, and high metabolic rate regions in a living organism wherein a radioisotope has been incorporated.

After emanating from the source 15, the radiation is subjected to a means for focussing the radiation, such as the lens, 18. The lens 18 directs the radiation to a detection device 19. The output of the detector is analyzed by a computer. The exemplary device 10 is a plane circular array of lens/detector assemblies 17 with the source 15 situated at the center 13 of the array, the detectors 19 positioned along the periphery of the array, and the focussing means 18 positioned approximately medially between the source 15 and the detectors 19. As noted supra, the detectors 19 comprise the periphery of the plane circular array and therefore are distally placed relative to the center 13 of the circular array and the focussing means 18.

Figure 2:
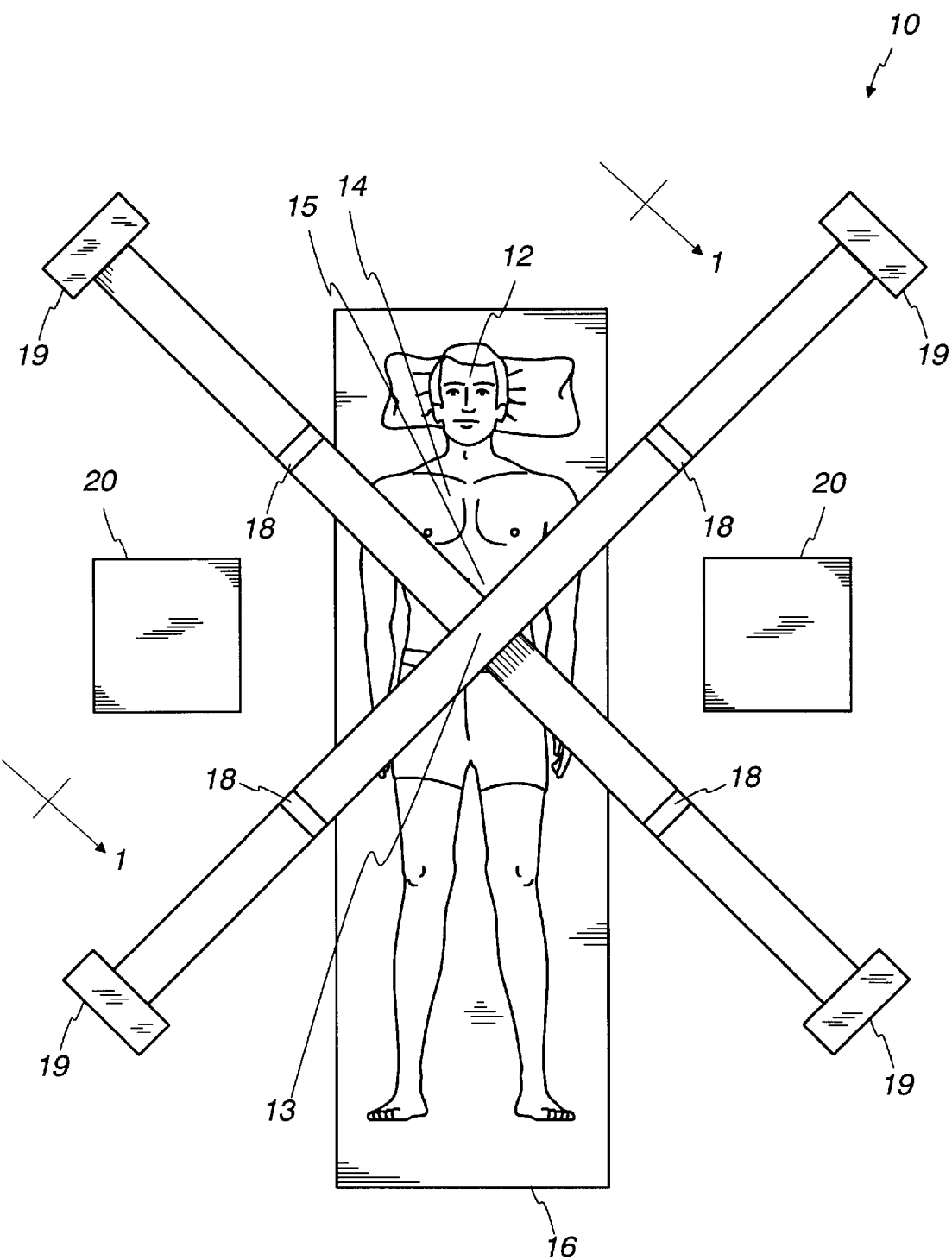
FIG. 2 is a cross-sectional, plan view of two intersecting arrays of lens/detector assemblies, in accordance with the present invention.

A three-dimensional scan of the source 15 can be accomplished with two lens/detector assemblies 17. FIG. 2 is an exemplary embodiment of a three-dimensional imaging system comprising two intersecting and concentric orthogonal arrays 10 of the lens/detector assemblies. The radiation source 15, resting on a movable platform 16, is located at the intersection of the two arrays at their common center 13 at the time of imaging. Prior to high resolution imaging operations, conventional scintillation counters 20 are provided for quick scan capabilities of the radiating area to approximately locate the source's position. For the sake of additional clarity, FIG. 1 is an elevational view of FIG. 2 taken along lines 1—1.

If the present invention is used as a medical imaging system, then the source 15 is a patient in whom a radioisotope has been injected. A reference source 14 of the same isotope is positioned at a suitable point on the patient's body and the location of the patient's tumor is measured with respect to the reference source 14. Imaging of an extended source is best accomplished by moving the movable platform 16 across the center 13 of the intersecting arrays 10. Alternatively, one could move the lens system relative to the source if means have been provided therefor.

The positions of the lenses, detectors, and a platform 16 containing the source 15 and the reference source 14 are monitored by conventional electronic sensors (not shown) and recorded and analyzed by a computer (not shown).

Lens/Detector Assembly Detail

Each lens/detector assembly 17 incorporates a plurality of movable focussing means (such as lenses 18) and detectors 19. The positions of the lenses, detectors and a platform 16 containing the source 15 are monitored by conventional electronic sensors (not shown) and recorded and analyzed by computer (not shown).

Figure 3:
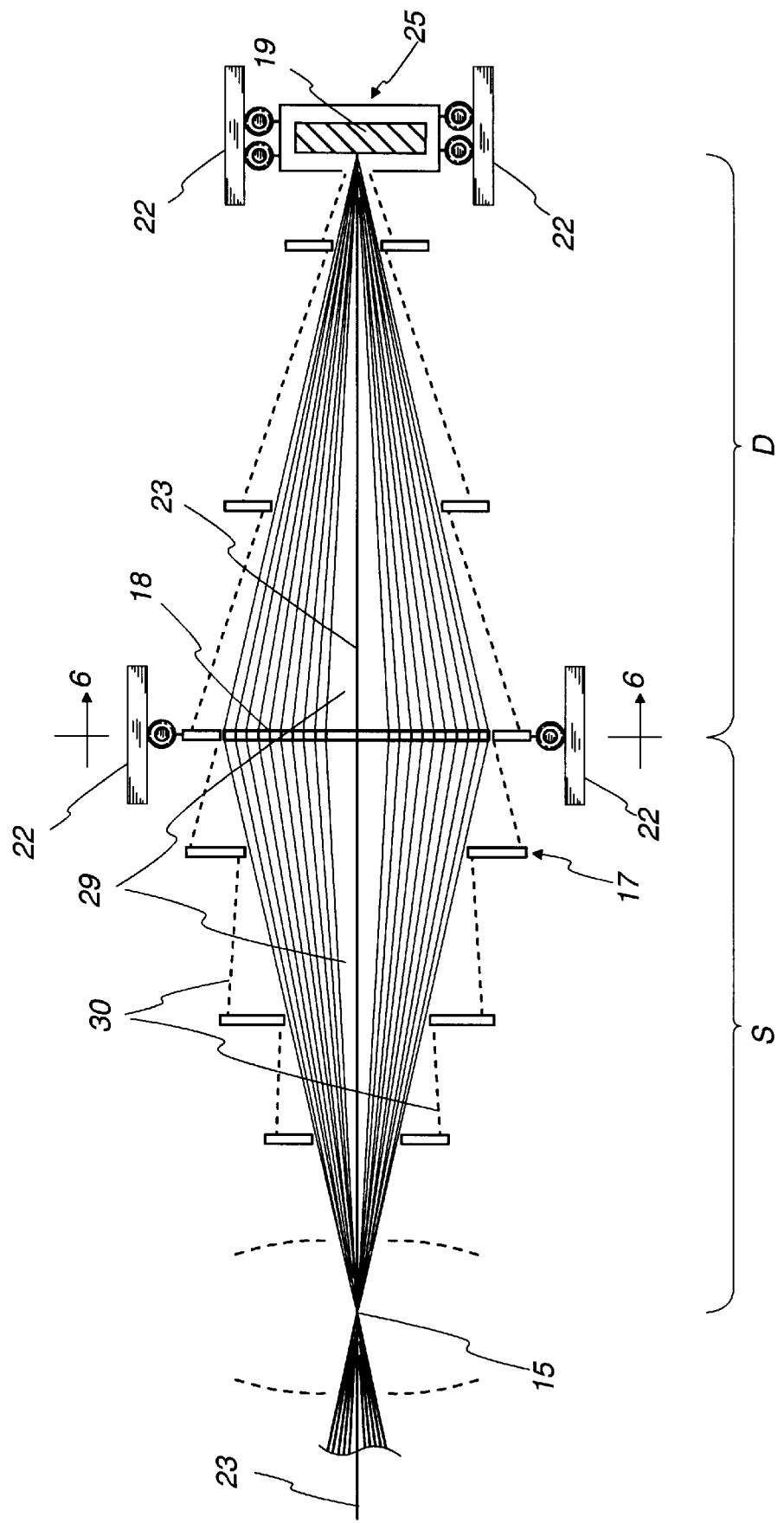
FIG. 3 is a cross sectional view of a lens/detector assembly as shown in FIG. 1, taken along lines 3—3, in accordance with the present invention.

FIG. 3 is a cross sectional view of FIG. 1 taken along lines 3—3 and presents a detailed depiction of the lens/detector assembly 17. Each lens/detector assembly 17 incorporates a plurality of movable focussing means (such as the lenses 18), detectors 19, and shielding around the detectors 19. Shielding is also placed along the longitudinal axis 23 of the assembly and longitudinally along the outside of the assembly. The axis and outside radiation shields 29, 30 respectively, are cone-shaped and mounted between the lens 18 and the source 15 and the lens and the detector 19. Generally, the axis and outside shields can be any convenient configuration such as cone- or cylindrically-shaped. Lead, iron, and brass are suitable shielding materials. S and D denote the lens-source, and the lens-detector distances respectively.

Lenses and detectors are mounted on tracks 22 equipped with electronic sensors. The tracks allow for independent axial movement of either or both the lens 18 and detector 19: Typically, the detector is moved in the same direction but twice as far as the lens. Generally, the detector 19 comprises a sodium iodide crystal, a zinc sulfide crystal, anthracene, or some other substance or combination of substances that scintillates when contacted with ionizing radiation. Also comprising the detector is a photomultiplier tube to monitor the scintillations as they occur.

Optionally, a 2×2 or 3×3 detector array is also suitable to enable a determination as to whether the source being imaged is on the axis of the lens or off the axis of the lens and if off-axis, to determine in which direction it is off-axis. In the case of the 2×2 array, the source is on axis when the counting rate in all four segments is equal. In the 3×3 array, is source is on axis when most of the radiation interacts with the central detector and the other detectors have equally weak count rates. The 3×3 array can also be used to obtain the lowest background possible. If the center detector is large enough to intercept all of the focused radiation when the source is on axis, then one needs to consider only the background in the center detector. Furthermore, an energy sum coincidence can be made between the center detector and the outside detectors that can increase the efficiency for detecting the full energy of the gamma ray, thus increasing the full energy count rate without increasing the background count rate. Thus, one has the efficiency of a large detector for detecting the full energy of the gamma ray, while retaining the low background counting rate of only the central detector.

The detector could also be a solid state detector made of silicon or germanium or a composite material such as CdTe. When radiation is absorbed by these detectors, positive and negative charges are generated that can be collected and measured with suitable electronics. These detectors have much better energy resolution and thus lower background counting rates. This would allow one to detect weaker sources. These detectors are, however, much more expensive.

Figure 4A:
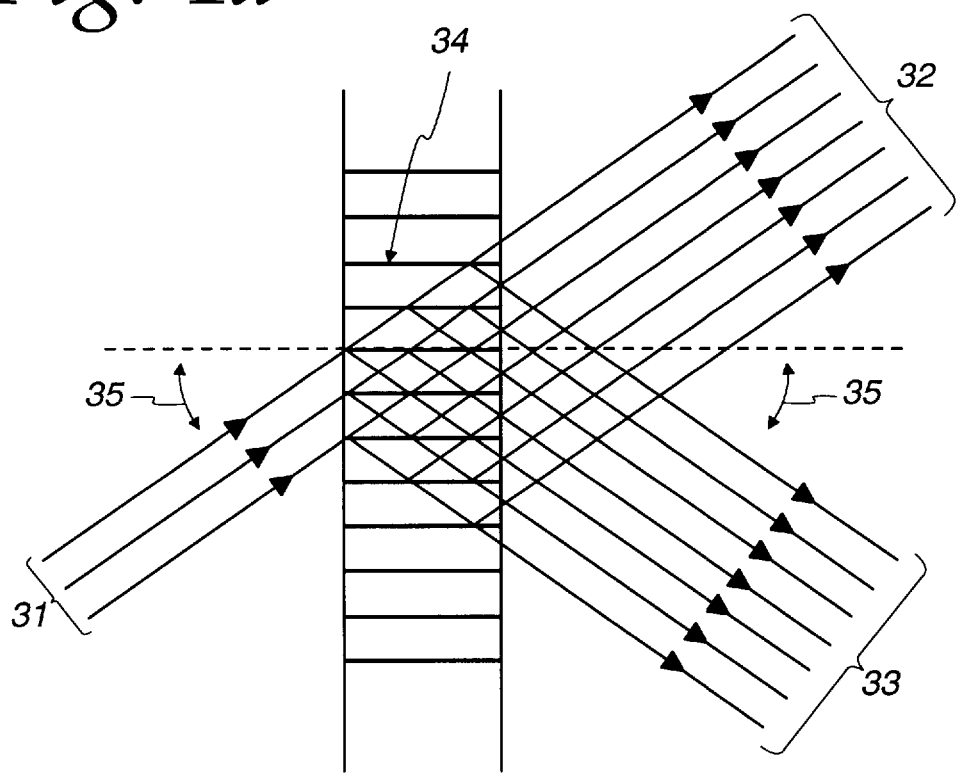
FIG. 4a illustrates the phenomenon commonly known as Laue Diffraction.

In order to focus x-ray and gamma radiation, the present invention utilizes the phenomenon of crystal diffraction which is illustrated in FIG. 4. FIG. 4a depicts the phenomenon known as Laue diffraction. The incident radiation beam 31 enters through one surface of a diffracting crystal. After interacting with a specific array of parallel atomic layers 34, the radiation beam is split into two beams, a transmitted beam 32, and a diffracted beam 33, with both beams exiting through a surface opposite to the one through which the radiation entered. Both the transmitted and the diffracted beams are produced by a coherent superposition of scatterings by atoms in the parallel crystal layers. The angle 35 between the radiation beam and the crystal layers is designated as p. The maximum fraction diffracted by crystals with some mosaic structure using Laue diffraction is 50%, with the remaining fraction being transmitted without deflection. Typically between $10^4$ and $10^7$ atomic layers are suitable to approach 50% diffraction. The actual number of layers depends on the wavelength of the gamma rays and the width of the mosaic structure of the crystal. In practice, the maximum diffracted beam is less than 50% because some absorption of the beam occurs as it passes through the crystal.

Figure 4B:
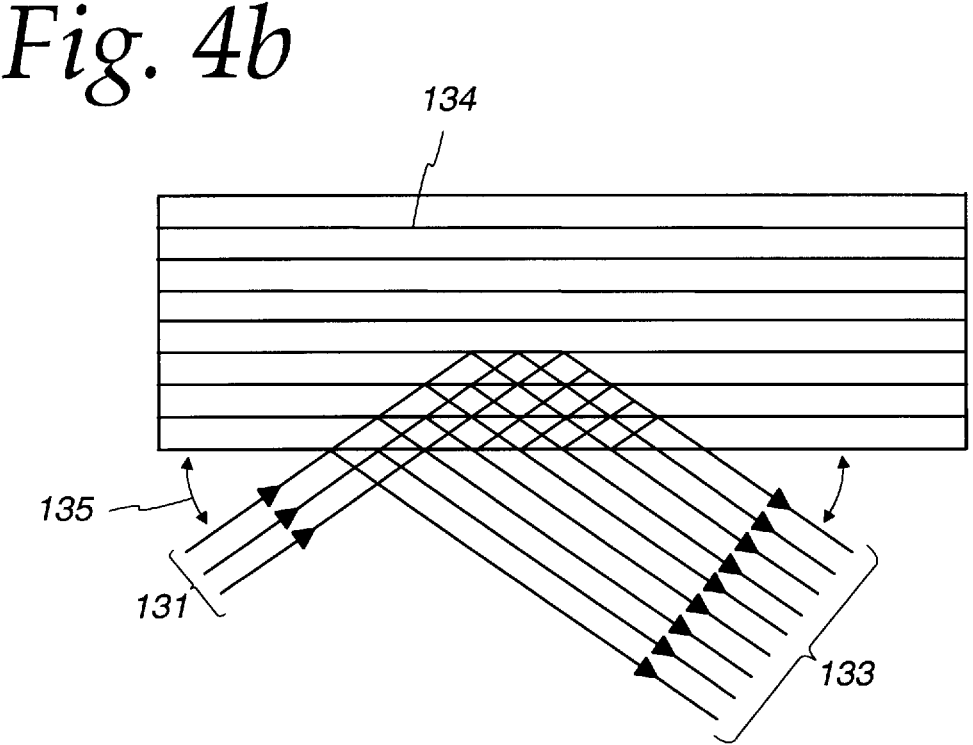
FIG. 4b illustrates the phenomenon commonly known as Bragg Diffraction.

FIG. 4b depicts the phenomenon known as Bragg diffraction acting upon an incident beam 131. After multiple scatterings with the atoms comprising a specific array of parallel atomic layers 134, the net outcome is the emergence of a "diffracted" beam 133, which contains nearly all of the incident energy. Some absorption of the radiation occurs during this process which continues until either the radiation is diffracted out of the crystal or is absorbed in the crystal. The angle 135 between the radiation beam and the crystal layers is designated as p. The diffracted beam exits through the same surface as the one through which the radiation entered. Again, the beam is produced by a coherent superposition of scatterings by atoms in the parallel crystal layers. Bragg diffraction is most effective for energies below 200 keV and the fraction diffracted can reach 90%.

For both Laue and Bragg diffraction, diffraction occurs only when the Bragg condition is obeyed, (equation 1):

$$\lambda = 2d_{hkl} \sin p \qquad (1)$$

where $\lambda$ is the radiation wavelength, $d_{hkl}$ the spacing between the atomic layers indicated by the Miller indices h,k,l and p the angle between the direction of the radiation beam and the atomic layers (one can convert energy E in keV to wavelength $\lambda$ in Angstrom units by using the relation $\lambda=12.397/E$). With perfectly parallel atomic layers, only rays within a few arc seconds of p will be diffracted (i.e., the "acceptance angle" is only a few seconds of arc), so that one can obtain a large diffraction efficiency only if the rays are nearly parallel, i.e. only if the source is very far away.

Figure 5A:
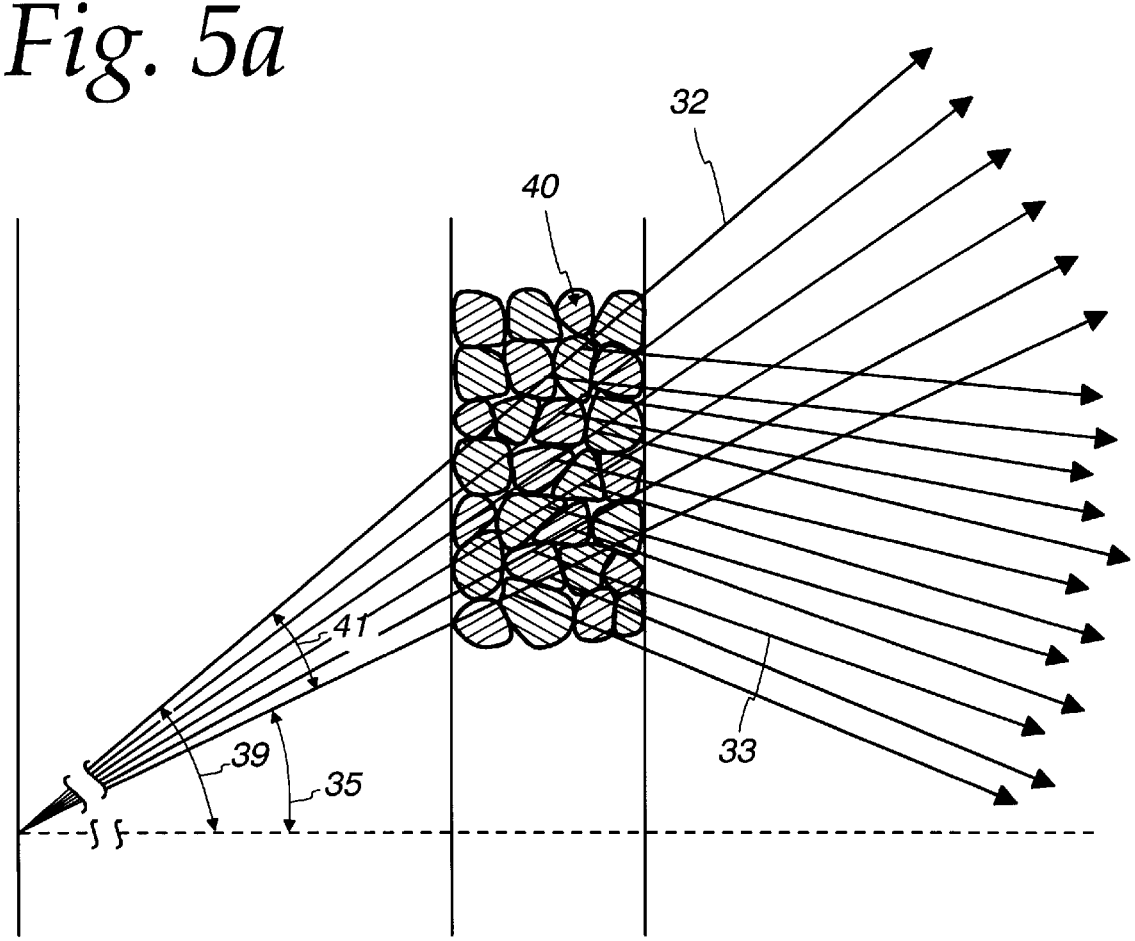
FIG. 5a illustrates the effect of crystal imperfections in Laue Diffraction.

As seen in FIG. 5, this problem can be overcome (i.e. the acceptance angle can be increased). FIG. 5a shows that for Laue diffraction, if imperfections are either naturally present or else artificially introduced within the crystal so that all the crystal planes are no longer parallel to each other, rays coming at different angles 39 will still find planes 40 for which the Bragg condition is obeyed. As seen in FIG. 5a the imperfections in the crystal give rise to a three dimensional mosaic structure. The angle 41 between the rays 35 with the lowest angle p and those 39 with the largest p is the acceptance angle.

Figure 5B:
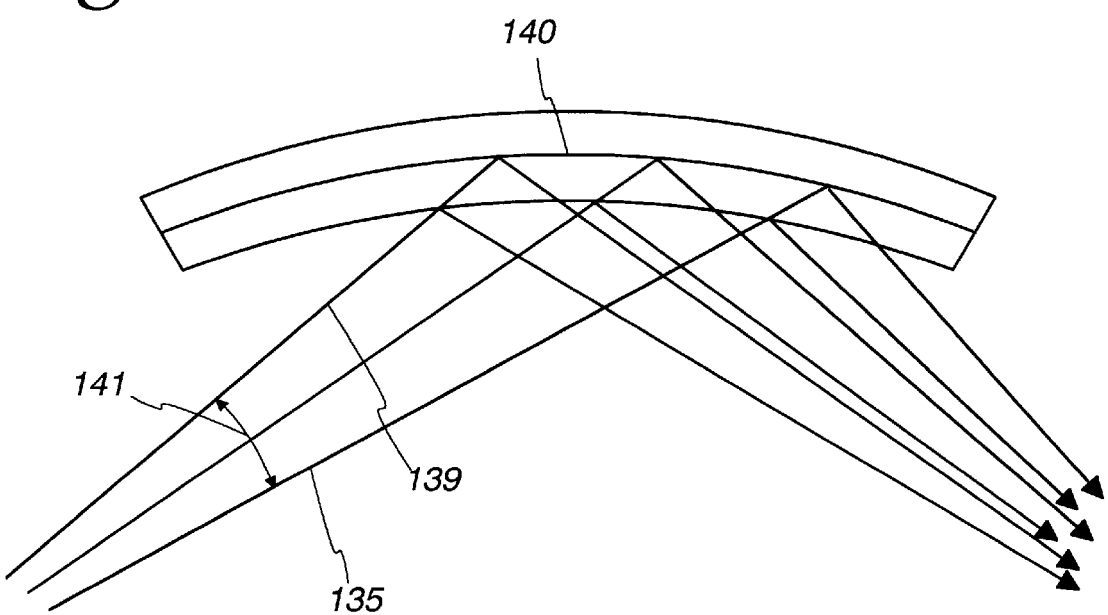
FIG. 5b is a detailed view of Bragg Diffraction from a bent crystal.

FIG. 5b shows that for Bragg diffraction the acceptance angle can be increased if the crystal is curved in the direction of the radiation beam. Rays coming at different angles 139 will still find planes 140 for which the Bragg condition will be obeyed. The angle 141 between the rays 135 with the lowest angle p and the rays 139 with the largest p is the acceptance angle. The curved shape of the crystals produces a significant focusing effect. The highest degree of focusing for Bragg diffraction occurs when the radius of curvature is equal to L / sin p , where L is the distance from the source to the lens. Furthermore, a mosaic structure in the crystal produces an increase in the acceptance angle in the same manner as described above for Laue diffraction.

Each crystal diffraction lens 18 utilizes a plurality of diffracting crystals. Possible crystalline materials include, but are not limited to, silicon, quartz, tin, molybdenum, germanium, and copper.

Figure 6:
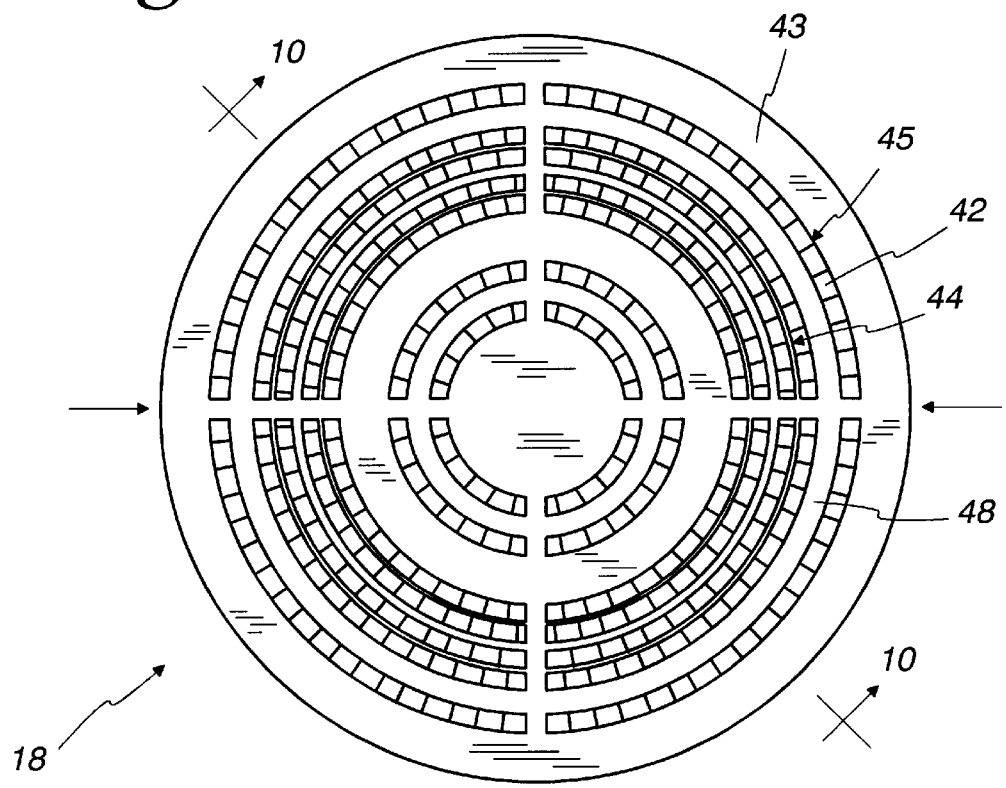
FIG. 6 is a plan view of a Laue crystal diffraction lens, in accordance with the present invention.

FIG. 6 is a view of FIG. 3 along lines 6—6 depicting a typical embodiment of a lens 18 in the Laue diffraction configuration. Each lens 18 comprises a support substrate 43 typically a metal plate. Stainless steel, brass, tungsten, and aluminum are suitable materials for the substrate 43 with stainless steel, brass, and tungsten having the advantage of better shielding the detector from radiation that was not diffracted by the crystals 42. Regions of the surface of the plate 43 define a series of apertures 44 arranged as concentric rings 45. Each ring contains a plurality of diffracting crystals 42 of the same material and orientation. The material and orientation are determined according to the procedure described below. The innermost ring has a diameter of about 2.7 cm and the outermost ring has a diameter of about 11.6 cm.

Figure 7:
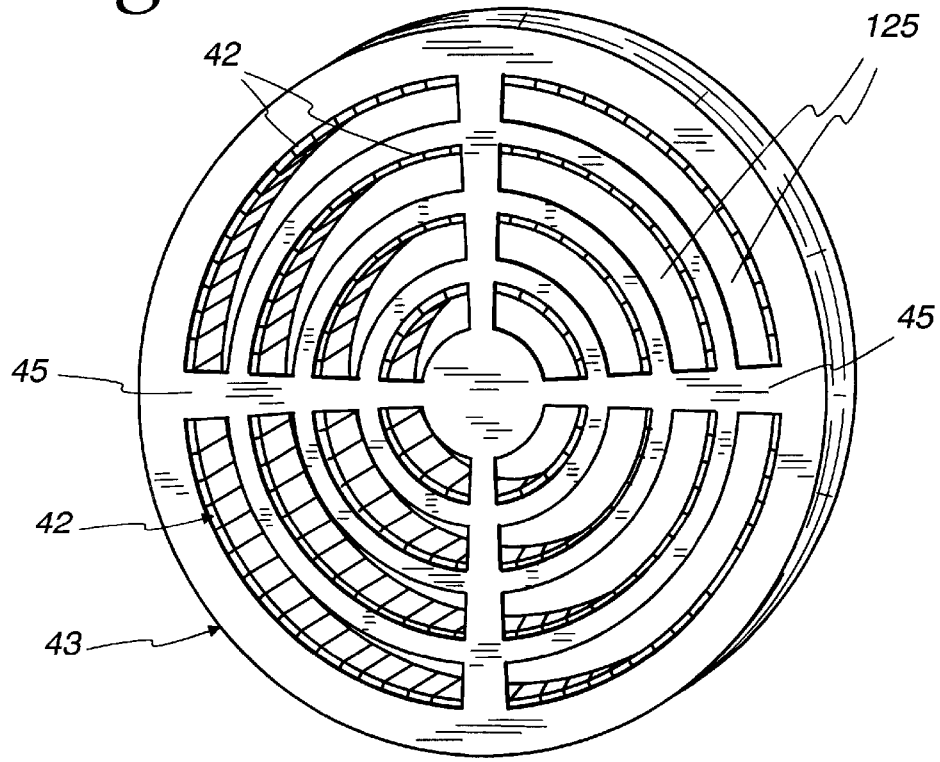
FIG. 7 is a plan view of a Bragg crystal diffraction lens, in accordance with the present invention.

FIG. 7 is a view of FIG. 3 along lines 6—6 and depicts a typical embodiment for lens 18 in the Bragg configuration. The significant difference is that the curved apertures 125 are much wider than the corresponding apertures 44 in FIG. 6a.

For both Laue and Bragg diffraction, the diffracting crystals are mounted onto the plate in such a manner that once mounted, all the crystals in a ring will be so oriented as to use the same set atomic layers to satisfy the Bragg condition. In a typical embodiment, the crystals in a given ring are all of the same material but crystals in different rings may be of different materials.

The first step in determining the material and orientation of the diffracting crystals is to select the energy of the radiation that will be observed and the focal length F of the focussing means 18 one wants to achieve. In the simplest embodiment of the invention, a single lens is utilized, in a lens/detector array 17, but a lens/detector assembly 17 having a plurality of lenses is also suitable.

Where lenses of focal length F1, F2, F3, etc . . . are placed in close proximity or contact with each-other, the focal length of the combination is given by equations 2 through 6.

Equation 2 gives the focal length for one lens, where p is the Bragg angle used in the lens and R is the radius of the crystal ring.

$$F = R/(\tan 2p) \qquad (2)$$

Equation 3 gives the focal length for two lens, where $p_1$ and $p_2$ are the Bragg angles used in the first and second lenses and $R_1$ and $R_2$ are the radii used in the first and second lens, respectively.

$$F_{12} = (R_1 - R_2)/\tan 2p_1 + R_2/\tan (2p_1 + 2p2) \qquad (3)$$

Equation 4 gives the focal length for three lenses, where $p_1$, $p_2$ and $p_3$ are the Bragg angles used in the first and second and third lenses and $R_1$, $R_2$ and $R_3$ are the radii used in the first, second and third lenses, respectively.

$$F_{123} = (R_1 - R_2)/\tan 2p_1 + (R_2 - R_3)/\tan (2p_1 + 2p_2) + R_3/\tan (2p_1 + 2p_2 + 2p_3) \qquad (4)$$

If the lenses are very close together, then the R's become approximately equal and the approximate formula for the focal length is given by equation 5.

$$F_{12 \ldots n} = R(\text{Ave})/\tan (2p1 + 2p_2 + \ldots + 2pn) \qquad (5)$$

If all of the Bragg angles are quite small, the focal length can be approximated by equation 6

$$1/F_{12} \ldots n = 1/F_1 + 1/F_2 + \ldots + 1/F_n \qquad (6)$$

The set of atomic layers to be used for each ring 45 is determined by the condition that all the rings must have the same focal length F. For rays near the lens axis (small p) the relation between lens-source distance S, lens-detector distance D, and focal length F is given approximately by equation 7.

$$(1/F = (1/S) = (1/D) \qquad (7)$$

In practice S and D as shown in FIG. 3 are both chosen to be 2F and the image formed onto the detector is about the same size as the source if the source is larger than the crystal elements in the crystal. If the crystals are bigger than the source, the image will be about twice the size of the crystals. Then the Bragg angle p is arctan R/(2F) where R is the radius of the ring. The Bragg condition yields the relation between the ring radius, focal length, radiation wavelength λ, and atomic layer spacing d, given by equation (8).

$$R/F = \tan [2 \arcsin(\lambda/2d_{hkl})] \qquad (8)$$

For F>>R, i.e., for small angles, Equation 8 yields $$d_{hkl} = \lambda F/R \qquad (9)$$

In practice, a gamma ray with a specific energy (and therefore wavelength λ) is selected. Then, the crystalline plane spacings of an available crystal are tabulated. This information is combined with the desired focal length F to arrive at the respective radii R for the crystal rings, pursuant to equation 10:

$$R = d_{hkl}/\lambda F \qquad (10)$$

Finally, the size of the crystals are chosen.

Alternately, λ is determined from the desired gamma ray energy, then F is chosen, and the available values of dhkl are identified, so that the values of R for the rings are suitable. Copper and germanium are suitable for radiation energies above 100 keV. Lower atomic number materials such as quartz, silicon, and beryllium are more suitable for low energy gamma rays (below 100 keV.)

Laue Diffraction Lens

In a preferred embodiment for a Laue diffraction lens, copper crystals grown at and obtainable from a facility such as the Institut Langevin-Langmuir (ILL) in Grenoble, France, are utilized. Copper crystals naturally exhibit enough imperfections in their crystal lattice so that their acceptance angle is of the order 200 to 500 seconds of arc, i.e. between 0.06 and 0.15 degrees. Heating and then compressing copper crystals increases the acceptance angle even further.

Figure 8A:
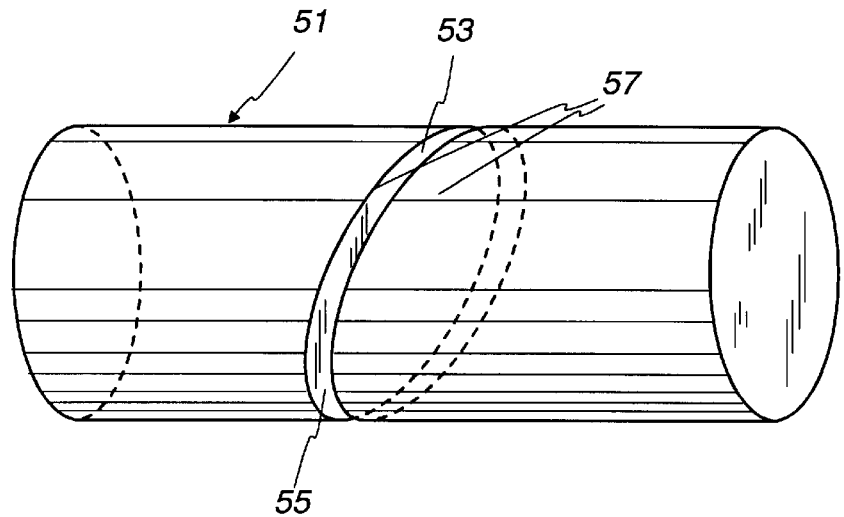
FIG. 8a depicts a procedure for cutting a slab of predetermined orientation from a crystal of known orientation supplied by a manufacturer.
Figure 8B:
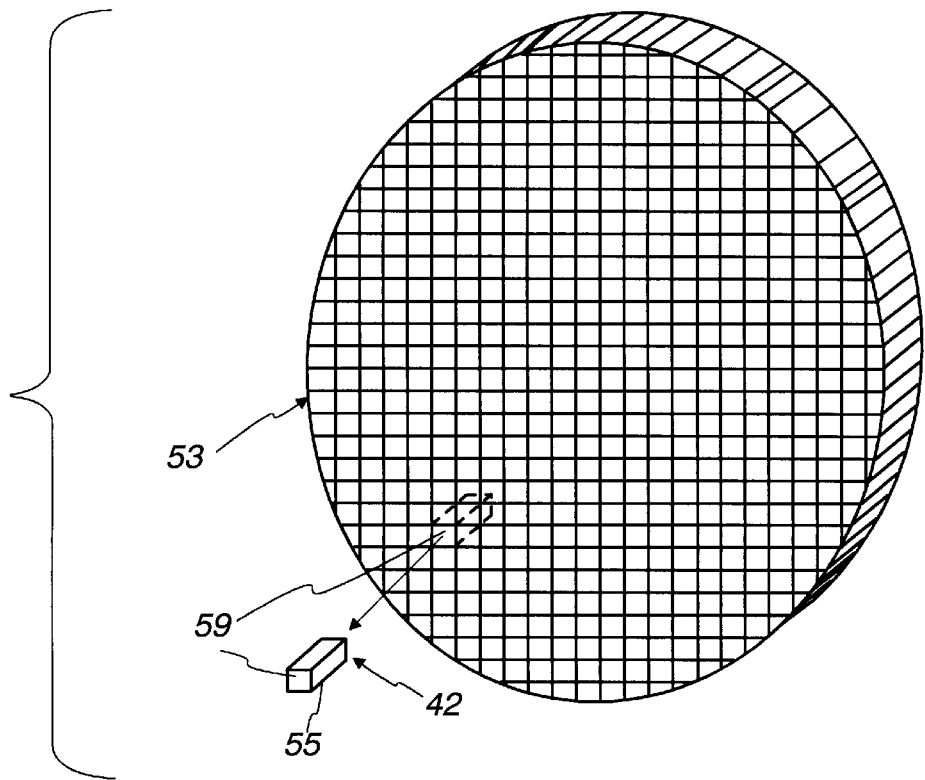
FIG. 8b depicts a procedure for cutting crystals of predetermined orientation, in accordance with the present invention.

Referring to FIG. 8a, ILL typically provides cylindrical copper crystals 51 of 10 cm. in diameter and 25 cm. long, with a predetermined crystal orientation. Thin slabs 53, of 2 to 3 mm thickness 55, are cut parallel to the planes 57 designated by the Miller indices that have been selected. As shown in FIG. 8b, the slabs 53 are then cut in turn into crystals 42 with faces 59 approximately 2 mm square. The faces 59 are perpendicular to the planes 57.

Mounting of the crystals 42 onto the plate 43 can occur in a variety of ways. One way is to first place the plate 43 against a rigid flat surface so that the flat surface is accessible though the concentric ring apertures 45. A number of crystals 42 are placed on the flat surfaces within the confines of the ring 45 with the face 59 of the crystals 42 (i.e., the face that corresponds to the plane selected as described supra) flush against the rigid flat surface. Enough crystals are placed in the ring to virtually fill the ring aperture. The crystals are then cemented together. Upon completion of the mounting procedure, the face 59 of the crystals that is perpendicular to the planes 57 whose Miller indices have been selected is perpendicular to the lens/detector assembly axis 23. (see FIG. 3) The area of this crystal face (2 mm square is suitable, as suggested supra) and the width of the mosaic structure determine the ultimate size of the image spot at the detector location 19. Crystal face 59 surface areas as small as 1 mm square are suitable. Copper and Germanium crystals are suitable for radiation energies above 100 keV. Lower atomic number materials such as quartz, silicon, and beryllium are more suitable for low energy gamma rays, i.e., below 100 keV.

Figure 9A:
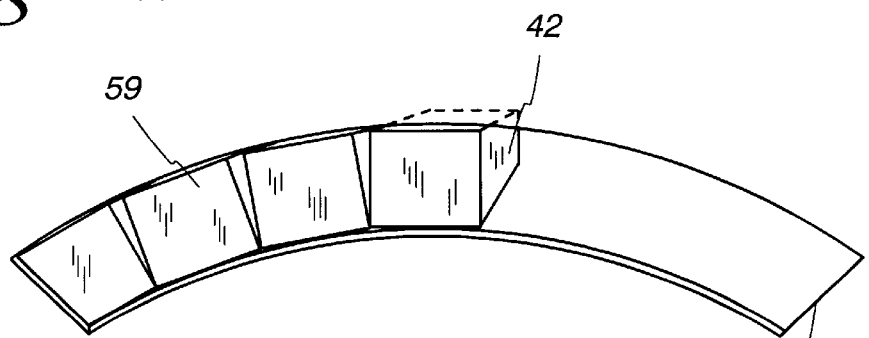
FIG. 9a–c are schematic views of the method for constructing a Laue diffraction lens out of a plurality of diffracting crystals, in accordance with the present invention.

FIG. 9a is a detailed view of one of the curved apertures 44 shown in FIG. 6 that contain the crystals 42. As shown, the crystals can be large enough to entirely fill the face of the aperture 44 or, if smaller than the aperture, they can be stacked on top of each other. In either configuration, once in place the crystals are then cemented into the containing means 44. In the instant embodiment, the containing means is the curved apertures. The face 59 of the crystals that is perpendicular to the planes 57 whose Miller indices have been selected is parallel to the plane of the substrate 43.

Figure 9B:
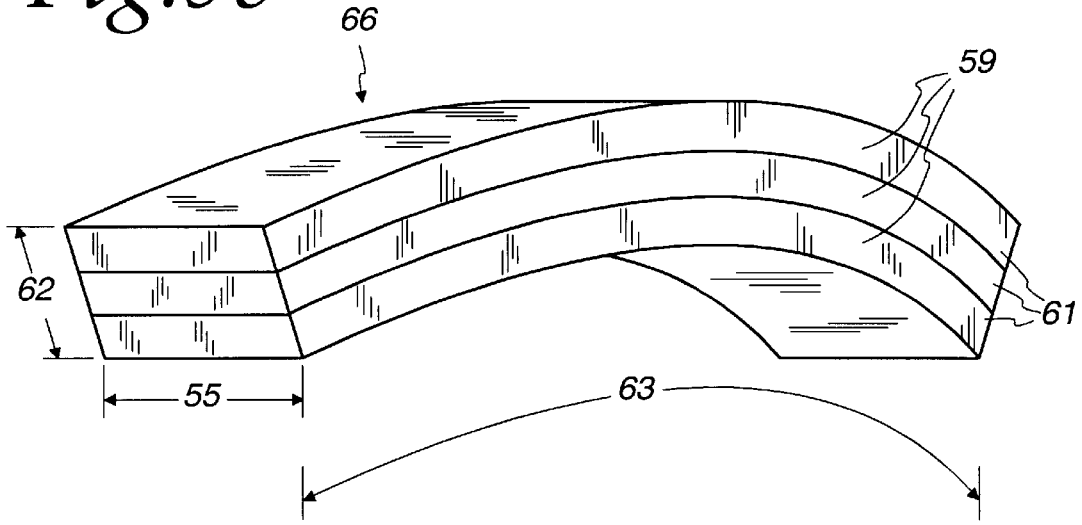

Alternatively, as shown in FIG. 9b, one may cut the crystals into thin strips 61 having a length 63 of perhaps 1 to 20 cm. The strips 61 are arranged in stacks 66 of a predetermined height 62 (for example 1 mm to 4 mm in height), and then bent into circular arc sections of the same radius as the ring 45 to be mounted therein. This procedure is more suitable when the crystalline materials are malleable.

Figure 9C:
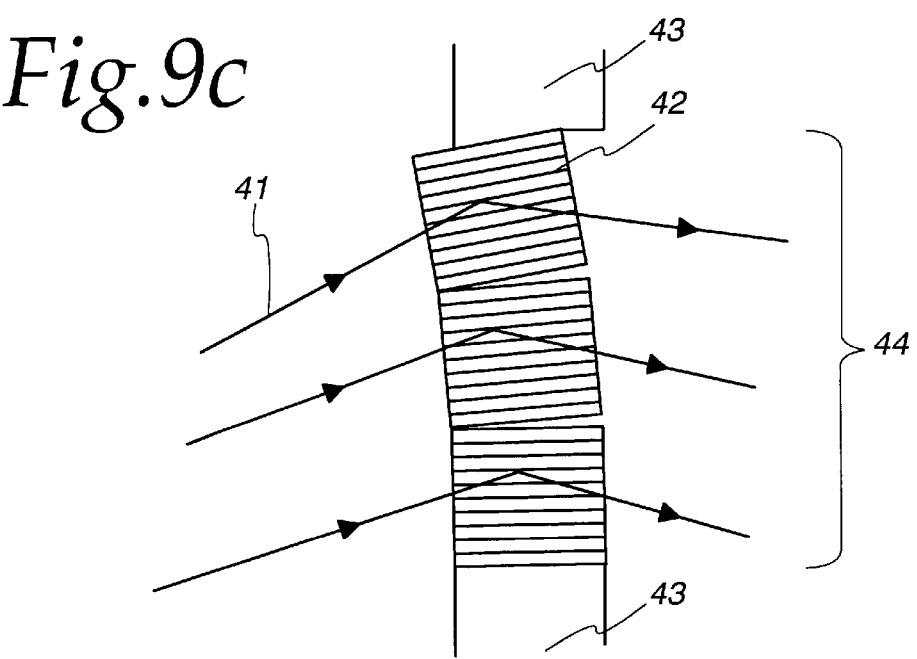

As an option, and as depicted in FIG. 9c, one may increase the fraction of the radiation that is diffracted onto the detector if the crystals 42 are cut with a wedge-like cross section and then stacked in the aperture 44 so that radiation 41 incident on each crystal is diffracted onto the detector. This wedge construction essentially increases the solid angle that the crystals in the lens can cover. As such, lens efficiency is concomitantly increased with a 2- or 3-fold increase in intensity of the diffracted beam.

Generally, crystals of malleable materials (e.g. copper, molybdenum and tin) or crystals of materials with low melting points are especially suitable in that they exhibit a high degree of mosaic structure. With suitable treatment, however, many other crystal types (and not just those from malleable elements) can be made to exhibit mosaic structure resulting in acceptance angels of 200 to 500 seconds of arc. Methods for introducing such mosaic structure include neutron irradiation, heating the crystal to near its melting point and then subjecting it to stresses or compression, subjecting the crystal to mechanical vibrations (e.g. sonic vibrations), and introducing impurities (i.e. dopants). Generally, the higher the atomic number of the material, the more efficient it is for diffraction of high energy gamma-rays.

Figure 10:
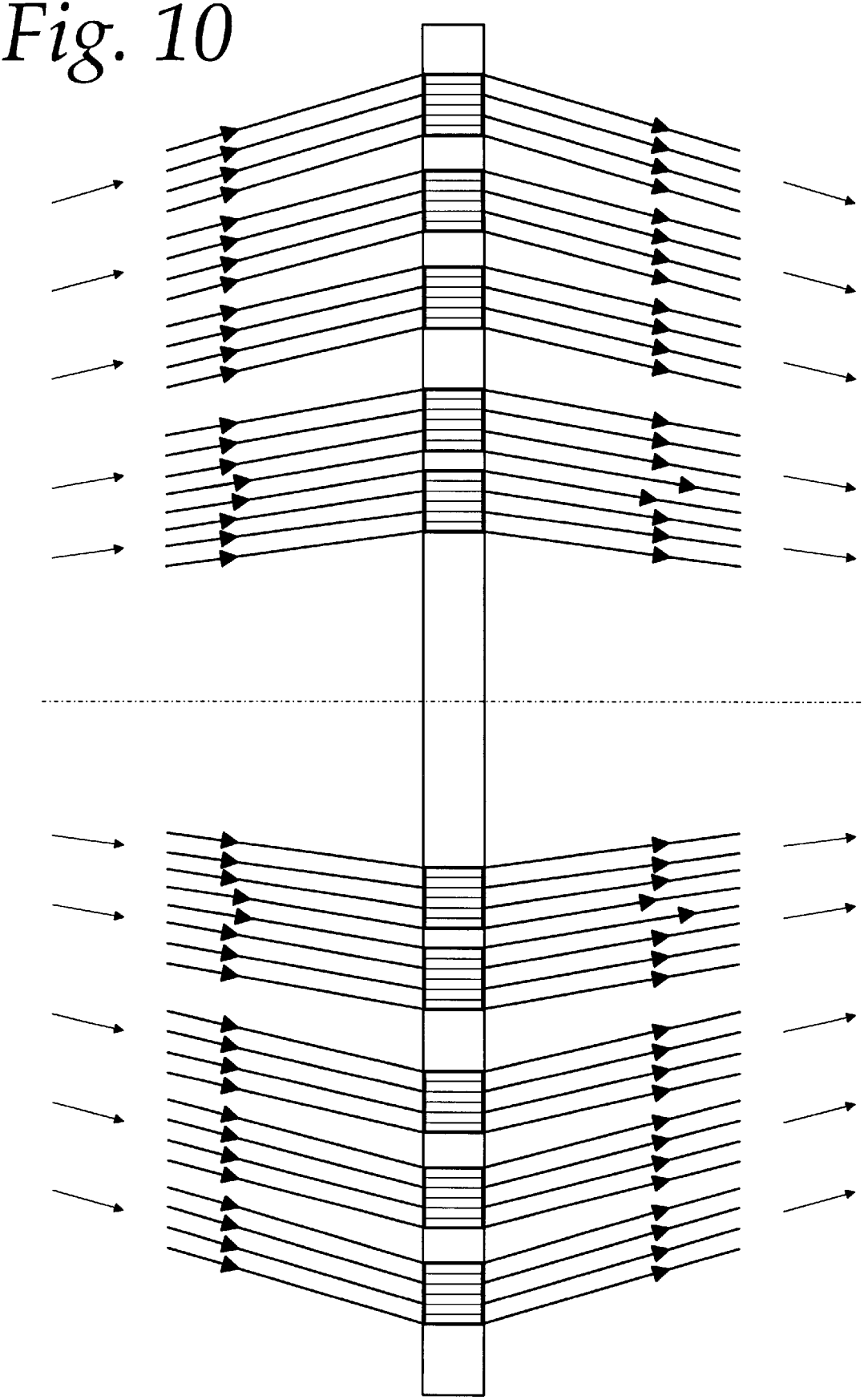
FIG. 10 is a view of FIG. 6 taken along line 10—10.

FIG. 10 is a cross-sectional view of a Laue diffraction lens 18 taken along lines 10—10 in FIG. 6.

Bragg Diffraction Lens

A wide variety of crystals are suitable for a Bragg diffraction. This is because the diffracted beam does not have to pass completely through the crystal and be reduced in intensity by absorption of the full thickness of the crystal. The diffraction efficiency for Bragg diffraction is determined by the ratio of the diffraction coefficient per unit length to the absorption coefficient per unit length. Since the ratio of these two quantities remains nearly the same for low gamma ray energies, the diffraction efficiency does not change as dramatically with changing energy as it does in the Laue diffraction case. For Bragg diffraction with bent crystals 42 (see FIG. 12 and FIG. 13), a large mosaic structure is not required in order to achieve a large acceptance angle. All that is required is that one be able to cut the crystals to form bendable strips of suitable dimensions. Exemplary dimensions are strips 1 to 2 mm wide, 0.5 to 2 mm thick, and 2 to 20 cm long. The crystal strips are then bent to a radius of 1 m or more, perpendicular to the crystal's long axis. The needed radius of curvature is equal to the distance from the source to the lens divided by sin p. The typical length of a strip is given by the width of the aperture 125 divided by sin p.

In the case of the bent Bragg crystals, the width of the mosaic structure controls the size of the field of view of the lens. Thus, one can adjust the size of the field of view independently of the size of the solid angle subtended by the crystals. Crystalline planes are selected and crystal strips are cut in much the same way as described in conjunction with Laue diffraction.

Figure 11:
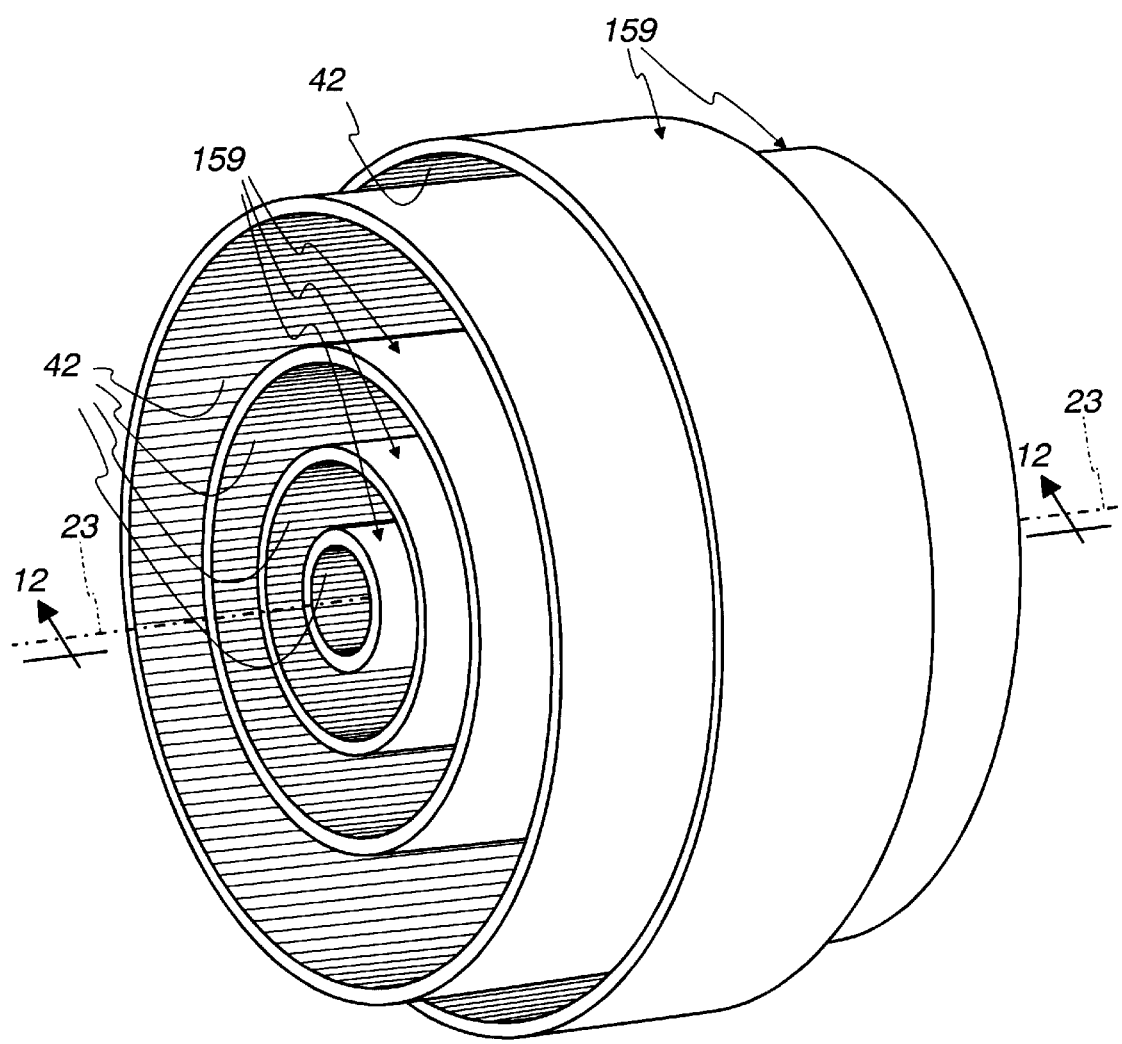
FIG. 11 is a three dimensional view of a Bragg diffraction lens.
Figure 12:
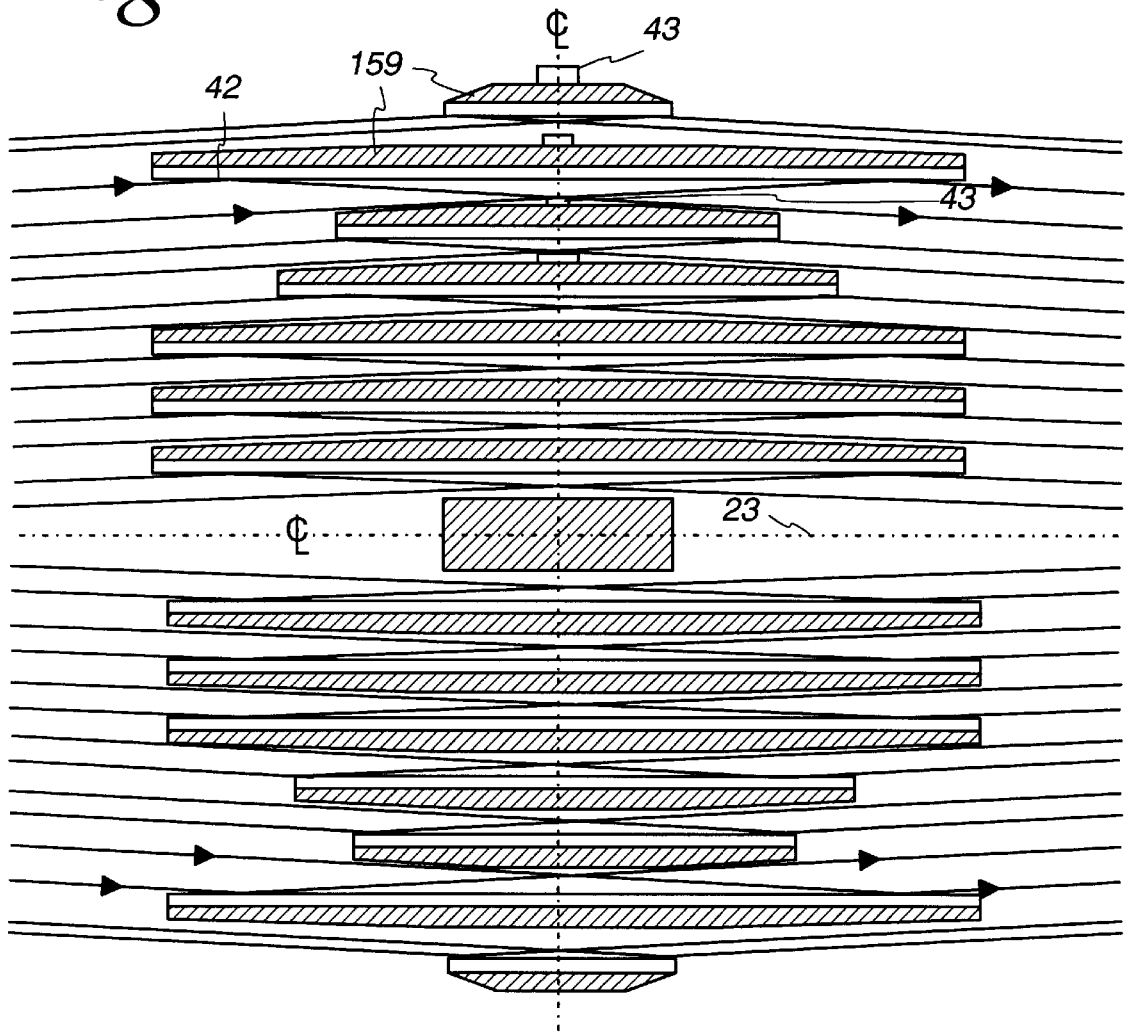
FIG. 12 is a view of FIG. 11 taken along lines 12—12.
Figure 13:
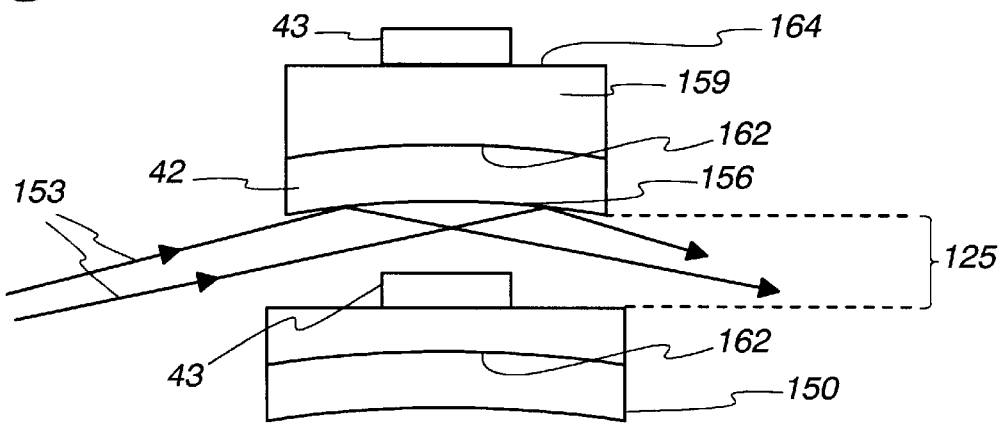
FIG. 13 is a detailed view of FIG. 12.

FIG. 11 is a three dimensional view of a Bragg lens. The Bragg crystals 42 are mounted on the concave surfaces of a plurality of coaxial cylindrical supports 159. FIG. 12 is a cross-sectional view of FIG. 11 along lines 12—12, and FIG. 13 is a detailed view of FIG. 12. FIG. 13 depicts how the crystals 42 are mounted on the supports 159. Said supports 159 are in turn mounted in a substrate 43 containing apertures 125 arranged as concentric rings 45. As can be seen in FIG. 13, the apertures 125 corresponding to each ring 45 are much wider than the crystal thickness 150 in order to allow the radiation beam 153 to impact upon all of the crystal face 156. The supports 159 that are provided for the bent crystals are shaped so that the radius of the support surface 162 matches that of the bent crystal. One such support can be a machined surface integrally molded, or removably attached to the substrate 43.

The use of bent Bragg crystals in the lens allows one to focus the diffracted beam from an individual crystal into a narrow line parallel to the diffraction planes and on the axis 23 of the assembly 17. This concentrates the diffracted beams from the full lens and makes it possible to use a smaller detector in the focal plane. The length 162 of the crystals 42 and the supports 159 is 2 to 20 cm in the direction of the beam 153. Generally, the longer crystals are closest to the lens axis 23, where the values of sin p are smallest. The length of the crystal strips are adjusted to obtain the maximum diffracted flux.

Scanning A Source And Formation Of An Image

The lens detector assembly achieves its best performance for sources located on or very near the axis of the assembly. When the source 15 is not situated on the axis of the assembly, the movable platform 16 is advanced until the source is positioned on the axis of the assembly.

In order to scan across the source 15, one may change the position of the body 12 using the means provided for moving the table 16. Alternatively, one may change the orientation of the lens/detector assemblies and adjust the source/lens and lens/detector distances as indicated by Equation 3 by means of the tracks 22 on which lenses and detectors are mounted. In yet another alternative, one can move the whole lens system relative to the source.

Also, equation 5 shows the focal length's dependence on the wavelength of the radiation. The lens 18 and detector 19 are mounted on tracks 22 allowing the use of a given lens to detect radiation of a different wavelength by adjusting lens-source and lens-detector distances as dictated by equation 3. Electronic sensors are mounted on tracks 22 and their signals are recorded and analyzed by the computer.

Instead of relying on tracks 22, imaging of radiation of different wavelengths can also be accomplished by using different lenses, and keeping the elements of the assembly stationary. For example, a source having a first energy can be scanned in toto by moving the Table 16 with respect to the center of the lens/detector arrays (see FIG. 1). If the device is to be used for gamma rays of a second energy, one can construct a plurality of different lenses using crystals with atomic spacings so chosen that one obtains the same focal length as the lenses used to focus the first source.

Signals from the detectors 19 are analyzed by a computer in conjunction with the data from the scintillation detectors 20 and those from the sensors on the movable platform 16 and the lens and detector tracks 22.

A variety of crystalline materials (Germanium, Silicon, Copper and Quartz) have been found by the applicant to be suitable for the fabrication of x-ray and gamma-ray lenses for energies of around 150 keV. Specifically, a prototype Laue crystal diffraction lens was constructed and tested early in the lens project at Argonne National Laboratory consisting of a ring of quartz crystals cubes, 5 mm×5 mm×5 mm mounted in a ring with a radius of 18 cm. This lens had a focal length for 140.4 keV gamma rays of 1.58 meters (m). This lens was also tested with the 59.54 keV gamma ray from $^{241}$Am where the focal length was 0.64 m. Tests were made at a series of distances between the lens and the source: 1.28 m, 1.92 m, 2.56 m, 3.20 m, and 3.84 m. These early tests laid the ground work for the development of this technology.

While the invention has been described with reference to details of the illustrated embodiment, these details are not intended to limit the scope of the invention as defined in the appended claims.

The embodiment of the invention in which an exclusive property or privilege is claimed is defined as follows:

1. A method for imaging a source of radiation comprising:
   a) using diffracting crystals to focus the radiation;
   b) analyzing said focused radiation to collect data as to the type and location of the radiation; and
   c) producing an image using the data.

2. The method as recited in claim 1 wherein the diffracting crystals are arranged to diffract the radiation to a predetermined focal point.

3. The method as recited in claim 2 wherein the arrangement of the crystals is determined by a predetermined energy of the radiation.

4. A method for imaging x-ray and gamma radiation comprising:
   a) supplying a plurality of sources of radiation;
   b) focussing said radiation onto a detector by means of diffracting crystals;
   c) analyzing said focused radiation to collect data as to the type and location of the radiation; and
   d) producing an image using the data.

5. The method as recited in claim 4 wherein the step of supplying said sources of radiation further comprises contacting a body with a radioisotope.

6. The method as recited in claim 4 wherein the step of supplying said sources of radiation further comprises contacting a tumor in vivo with a radioisotope.

7. A method for imaging x-ray and gamma radiation comprising:
   a) supplying a plurality of sources of radiation;
   b) focussing said radiation onto a detector;
   c) analyzing said focused radiation to collect data as to the type and location of the radiation; and
   d) producing an image using the data; wherein the step of focussing said radiation further comprises arranging crystals to diffract said radiation to a predetermined focal point.

8. The method as recited in claim 7, further comprising selecting said crystals to contain random imperfections.

9. The method as recited in claim 7 wherein the step of arranging said crystals further comprises cutting said crystals into thin slabs and bending said cut crystals to assume the shape of circular arcs.

10. The method as recited in claim 4 wherein the step of analyzing said focused radiation further comprises directing said focused radiation to a plurality of detectors with a resolution of from 2 mm to less than 8 mm.

11. The method as recited in claim 4 wherein the step of analyzing said focussed radiation further comprises directing said focussed radiation to a plurality of detectors having a resolution of 2 mm.

12. The method as recited in claim 4 wherein the step of supplying a plurality of said sources of radiation further comprises placing at least one of said sources at precisely known locations.

13. A device for imaging a plurality of sources of x-ray and gamma-ray radiation comprising:
   a) a means for locating the sources of radiation;
   b) a plurality of diffracting crystals for focussing the radiation emanating from the located sources and directing it to a detector;
   c) a means for analyzing said directed radiation to collect data as to the type and location of the radiation; and
   d) a means for converting the data to an image.

14. The device as recited in claim 13 wherein the means for locating the sources is a plurality of scintillation devices.

15. The device as recited in claim 13 wherein the diffracting crystals form a plurality of lenses.

16. The device as recited in claim 14, where the diffracting crystals are movable relative to the plurality of sources.

17. The device as recited in claim 13 wherein the sources are movable relative to the plurality of diffracting crystals.

18. The device as recited in claim 13 wherein the radiation sources are radioisotopes.

19. A device for imaging a plurality of sources of x-ray and gamma-ray radiation comprising:
   a) a means for locating the sources of radiation;
   b.) a means for focussing the radiation emanating from the located sources and directing it to a detector;
   c.) a means for analyzing said directed radiation to collect data as to the type and location of the radiation; and
   d.) a means for converting the data to an image; wherein the means for focussing the emitting radiation is a plurality of lenses, each lens comprising a plurality of crystals and wherein the crystals are oriented so as to diffract radiation of a predetermined energy to the same focal point.

20. A device for imaging a plurality of sources of x-ray and gamma-ray radiation comprising:
   a) a means for locating the sources of radiation;
   b.) a means for focussing the radiation emanating from the located sources and directing it to a detector;
   c.) a means for analyzing said directed radiation to collect data as to the type and location of the radiation; and
   d.) a means for converting the data to an image; wherein the means for focussing the emanating radiation is a plurality of lenses, each lens comprising a plurality of crystals and wherein the crystals are mounted in concentric rings onto a substrate.

21. The device as recited in claim 20 wherein the substrate is opaque to gamma-radiation and x-ray radiation.

22. The device as recited in claim 20 wherein the concentric rings onto a substrate are axially juxtaposed medially to the detector and the sources to form an assembly having a longitudinal axis that is perpendicular to the plane formed by the substrate.

23. The device as recited in claim 22 wherein a plurality of assemblies are juxtaposed relative to each other in a plurality of concentric intersecting circular arrays wherein the center of each of the arrays coincides with the location of a source of radiation.

* * * * *